(12) United States Patent
Tas

(10) Patent No.: US 7,381,262 B2
(45) Date of Patent: Jun. 3, 2008

(54) METHOD OF PREPARING POROUS CALCIUM PHOSPHATE GRANULES

(75) Inventor: Ahmet Cueneyt Tas, Central, SC (US)

(73) Assignee: Biomet Deutshland GmbH, Berlin (DE)

(*) Notice: Subject to any disclaimer, the term of this patent is extended or adjusted under 35 U.S.C. 154(b) by 315 days.

(21) Appl. No.: 10/513,596

(22) PCT Filed: Apr. 7, 2003

(86) PCT No.: PCT/EP03/03583

§ 371 (c)(1),
(2), (4) Date: May 24, 2005

(87) PCT Pub. No.: WO03/093196

PCT Pub. Date: Nov. 13, 2003

(65) Prior Publication Data

US 2005/0260115 A1   Nov. 24, 2005

(30) Foreign Application Priority Data

May 6, 2002   (EP)   .................... 02010043

(51) Int. Cl.
*C04B 12/02* (2006.01)
(52) U.S. Cl. .................................................. 106/690
(58) Field of Classification Search ................ 423/305, 423/307, 308, 311; 106/690
See application file for complete search history.

(56) References Cited

U.S. PATENT DOCUMENTS

| | | | | |
|---|---|---|---|---|
| 4,429,691 A | * | 2/1984 | Niwa et al. | 606/77 |
| 4,859,383 A | | 8/1989 | Dillon | |
| 5,525,148 A | * | 6/1996 | Chow et al. | 106/35 |
| 6,117,456 A | * | 9/2000 | Lee et al. | 424/602 |
| 6,306,297 B1 | * | 10/2001 | Ichitsuka et al. | 210/198.2 |

FOREIGN PATENT DOCUMENTS

JP   04240167   8/1992

OTHER PUBLICATIONS

Database WPI; Week 20004I; Derwent Publications Ltd., London GB, no date.

* cited by examiner

*Primary Examiner*—Wayne A. Langel
(74) *Attorney, Agent, or Firm*—Millen, White, Zelano & Branigan, P.C.

(57) ABSTRACT

The invention describes a method of preparing macroporous calcium phosphate granules with NaCl porogen technique, wherein a calcium phosphate self-setting cement powder is mixed with 30 to 80 wt % NaCl. The calcium phosphate granules comprise macro- and micropores communicating with one another substantially throughout the body with a porosity of 40% or more and having the same mineral as those of human bones. Said granules are used as a substitute or repairing material for bone, carrier material for drug delivery and gradual release system.

12 Claims, 1 Drawing Sheet

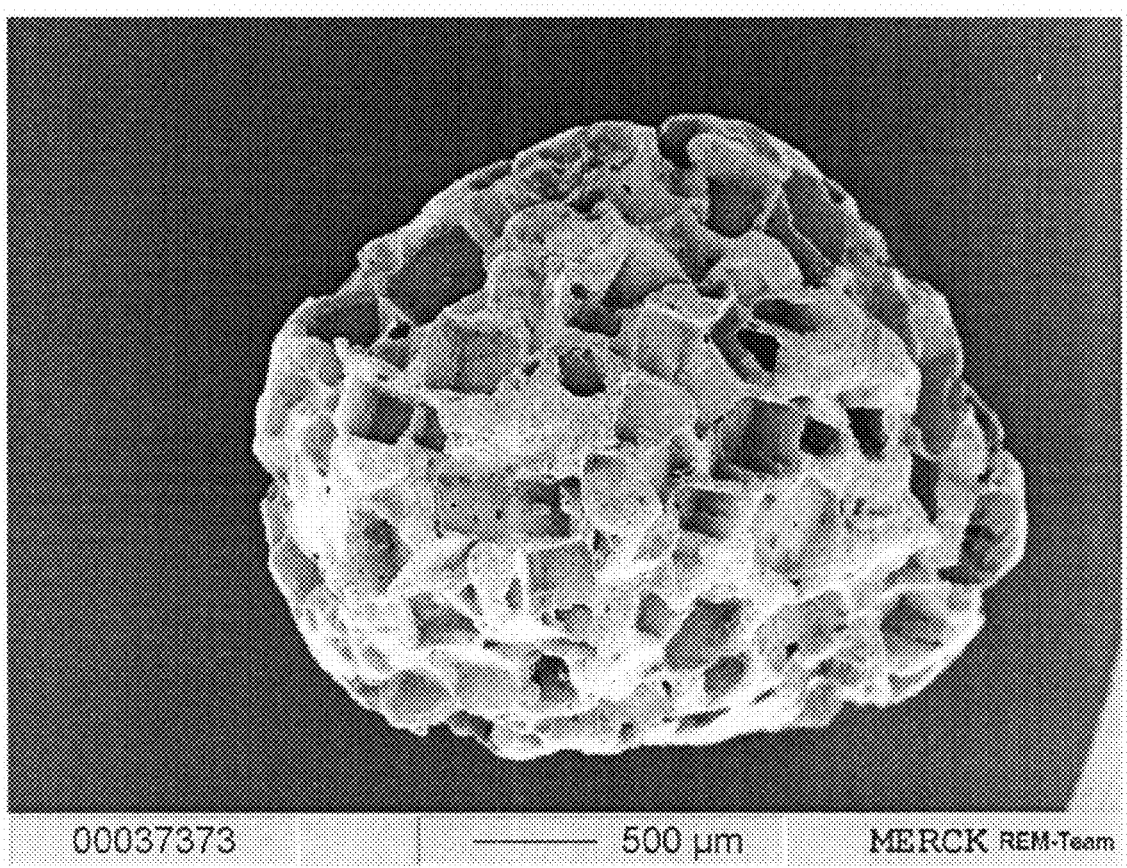

METHOD OF PREPARING POROUS CALCIUM PHOSPHATE GRANULES

The invention relates to a simple method of preparing porous calcium phosphate granules with the NaCl porogen technique.

Insertion (or presence) of macropores (pores>100 micron in size or nests, which allow sites for living cell attachments) into calcium phosphate bone cements increase their resorption time (while the bone remodelling around the implant is taking place within the first few months) upon their implantation into the body. In that sense, making easily applicable (by the surgeon) bone cement materials with a significant amount of macropores in them is quite a hot topic in the field of bioceramics (ceramics which are designed, synthesized and used in biological and clinical applications).

Hong-Ru Lin et al. (J. Biomed. Mater Res. (Appl. Biomater.) 63: 271-279, 2002) describes a mixture of $NH_4HCO_3$ and NaCl particles used as a porogen additive to fabricate highly macroporous biodegradable poly(lactic-co-glycolic acid) scaffolds. A two-step salt-leaching process was performed after the sample had become semi-solidified. A disadvantage of this method, when its application for calcium phosphate-based cement compositions considered, is the fact that the use of basic salts such as ammonium bicarbonate destroys the deliberately adjusted chemical composition of the cements, especially during the following washing steps.

There are several other (porogen) techniques which employ the initial mixing of calcium phosphate ceramics together with organic (or even inorganic) materials (porogens), followed by heating them at sufficiently high temperatures (100° to 1400° C.) to volatilize the porogen components, and forming gas bubbles in their places, which then provide the desired porosity to the product.

Another decent porogen technique for preparing porous calcium phosphate granules is using "ice crystals" as the porogen (instead of NaCl or any other thing), but on a larger scale production, the precise control of the size and morphology of those ice crystals (without significantly sacrificing the mechanical strength/stability of the final granules) requires quite a high expenditure in terms of equipment and cold environments to be acquired/set at the production site.

An object of the present invention is to provide a simple method for preparing macroporous calcium phosphate granules via NaCl porogen technique, which avoids the above-mentioned disadvantages from the prior art.

Upon further study of the specification and appended claims, further objects and advantages of this invention will become apparent to those skilled in the art.

These objects are achieved by a method of preparing macroporous calcium phosphate granules characterized in that the method comprising the steps of:
a) mixing a calcium phosphate self-setting cement powder and 30 to 80 wt % sodium chloride
b) wetting the powder with a mixture of ethanol and $Na_2HPO_4$ aqueous solution as specific setting solution of the cement.
c) kneading the wet powder body to form a cake
d) sieving the wet cake in an automatic sieving machine (with multiple sieves) to in situ form granules of desired sizes
e) leaching out of the sodium chloride (porogen) with water
f) placing the granules in dilute $Na_2HPO_4$ solution
g) washing the granules with water
h) drying the obtained granules.

The porous calcium phosphate granules (size range 0.5 to 6 mm) are used as a substitute, or repairing material for bone, carrier material for drug delivery and gradual release system.

The present porous granules of a self-setting calcium phosphate cement are produced by preparing a powder mixture of the said calcium phosphate cement with sodium chloride (preferred is a weight ratio of NaCl powder to cement powder=1.7 to 1.8, more preferred 1.75), wetting and kneading it first with a mixture of its setting accelerator solution (preferably with a Liquid (in ml)-to-cement powder (in grams) ratio of 0.30) and a smaller amount of ethanol, and granulating the paste in an automatic sieving machine with multiple sieves of desired granule sizes, before the cement setting to take place in the first 8 minutes of mixing with the above solution, followed by first dissolving out the sodium chloride at room temperature in pure water, second rinsing the formed granules in a dilute hydrochloric acid solution to create interconnectivity among the pores of the granules, and third immersing the granules in the cement's own setting solution at the human body temperature to increase their mechanical strength, finally followed by drying and sieving of the formed granules.

It is advantageous using NaCl, because human plasma and human body fluids contain 5.8 g of NaCl per liter of them. Therefore, NaCl is an inorganic material, which is perfectly compatible with the human plasma.

A further advantage of the present method is that it does not employ any high temperature treatment (to form porosity), which otherwise could easily destroy the precise balance (amount and composition-wise) to be retained between the calcium phosphate constituents.

A further advantage of the said method is that it leaves behind its footprint. NaCl crystals are cubic due to their crystallographic nature. Moreover, NaCl crystals do exhibit dislocation steps or kinks on their surfaces (readily visible with scanning electron microscopes) and the pores left behind (after dissolving out those NaCl crystals) in the calcium phosphate cement matrix are like the "replicas" of those crystals, and the product can then easily be identified (as depicted in the FIGURE) according to its manufacturing process.

Advantageous is also that the time of processing (i.e. the time calcium phosphate powder and NaCl powder are in contact with one another as an intimate mixture) is extremely short, within the following 20 minutes, in the washing step, NaCl is taken out of the system. Moreover, the method is, in terms of the manufacturing costs on a larger scale, cheap.

The present method can be used with any "self-setting calcium phosphate cement" already available. Suitable cements, which can be used, are: powder mixtures of calcium phosphate "species" (one or more of them to be present in the final powder body) or "phases" or "constituents"

a) Amorphous calcium phosphate (ACP)
b) MCPM (monocalcium phosphate monohydrate: $Ca(H_2PO_4).H_2O$)
c) TTCP (tetra calcium phosphate: $Ca_4(PO_4)_2O$)
d) alpha-TCP (tricalcium phosphate: $Ca_3(PO_4)_2$)
e) beta-TCP ($Ca_3(PO_4)_2$)
f) DCPD (dicalcium phosphate dihydrate: $CaHPO_4.2H_2O$)
g) DCPA (dicalcium phosphate anhydrous: $CaHPO_4$)
h) HA (calcium hydroxyapatite: $Ca_{10}(PO_4)_6(OH)_2$)
i) Calcium carbonate ($CaCO_3$)

j) Calcium hydroxide ($Ca(OH)_2$) and (as minor components in a calcium phosphate matrix)
k) biocompatible polymers (such as polylactic acid, PLA or polylacticglycolic acid, PLGA or polymethylmetacrylate, PMMA)
l) biocompatible silicates (such as silicate compounds to be formed out of the quaternary system of $Na_2O$—$P_2O_5$—$CaO$—$SiO_2$)

prepared/mixed (with one or more of the above components) with a variable Ca/P over the range of 1.0 to 2.0, more preferably over the range of 1.2 to 1.55, when mixed with a proper setting solution (ranges from pure water to dilute phosphoric or citric acid solutions and even to alkali phosphate dilute aqueous solutions, i.e., the setting solutions can either be acidic, neutral or basic with respect to their pH values), sets in a relatively short time at the human body temperature to gain a significant strength (variable in the range of 5 MPa to 100 MPa).

Preference is furthermore given to a biocement (as calcium phosphate self-setting cement powder) of 50 to 70% α-TCP, 2 to 9% HA, 20 to 30% DCPA and 5 to 10% $CaCO_3$.

The calcium phosphate granules have pore sizes in the range of 0.5 to 6 mm, preferably about 2 to 3 mm.

The porosity of the present granules is 30 to 70%, preferably about 40 to 50%.

Preference is furthermore given to the calcium phosphate cement powder, which is mixed with 60 to 65 wt % sodium chloride powder.

It is further preferred that 60 to 70 wt % of sodium chloride powder having particle sizes less than 0.25 mm and the remaining 30 to 40 wt % having particle sizes greater than 0.25 mm.

The macropores of the calcium phosphate granules have middle diameters of 50 to 1000 microns, preferably about 50 to 400 microns.

The invention is described in detail below in terms of the following working example.

In the foregoing and in the following examples, all temperatures are set forth uncorrected in degrees Celsius; and, unless otherwise indicated, all parts and percentages are by weight.

The FIGURE shows an electron microscope photograph of the formed granules.

WORKING EXAMPLE

Preparation of the Macroporous Calcium Phosphate Granules

To prepare the macroporous calcium phosphate granules, Calcibon® powder and NaCl powder in a molar ratio of 1:6.2, corresponding to 40 g: 70 g are mixed in dry form in a plastic box in a Turbula mixer for 90 minutes (without grinding balls in the box). 60 wt % of NaCl powder used above have particle sizes less than 0.25 mm, and the remaining 40 wt % of it with particle sizes greater than 0.25 mm. The powder mixture is then wetted and thoroughly kneaded with a premixed solution of 6.7 ml ethanol plus 12 ml aliquot of 3.5 wt % $Na_2HPO_4$ solution in a bowl-like container for 3 to 4 minutes. The wetted cement+NaCl cake is then immediately placed on an automatic sieving machine which has the sieves in desired mesh opening sizes to exactly yield the desired granule sizes. Sieving is performed and completed in 2 minutes. Humid granules of desired sizes are thus produced in situ on the selected sieves. Granules of different sizes are left to dry in the ambient atmosphere and temperature for about 1 hour. Next, the porogen (NaCl) is leached out with water (water must be replenished continuously) at room temperature (RT) (total residence time of the granules in the washing water must at least be 72 hours). The washed granules are dried at 50-60° C. for 24 hours and placed in 1 wt % $Na_2HPO_4$ solution at 37° C. (ratio of "weight of granules (in gram)" to "liquid volume (in ml)" must be 0.04 (to increase the mechanical strength of the granules), followed by washing with water and drying at 50-60° C.

EDXS analysis performed on the final, dried granules showed that they did not contain any Na and Cl ions originating from the use of NaCl, after washing with water.

The formed granules have a density of 1.6 g/cm³, and they have a water absorption percentage of 150.

The invention claimed is:

1. A method of preparing macroporous calcium phosphate granules comprising:
   a) mixing a calcium phosphate self-setting cement powder and 30 to 80 wt % sodium chloride,
   b) wetting the mixture from a) with ethanol containing $Na_2HPO_4$ solution,
   c) kneading the mixture from b),
   d) in situ forming of humid granules on a sieve machine,
   e) leaching out the sodium chloride with water,
   f) placing the granules in $Na_2HPO_4$ solution,
   g) washing the granules with water and
   h) drying the obtained granules.

2. The method according to claim 1 wherein said calcium phosphate powder is a biocement of 50 to 70% α-TCP, 2 to 9% hydroxylapatite, 20 to 30% dicalcium phosphate anhydrous and 5 to 10% $CaCO_3$.

3. The method according to claim 1 wherein the macroporous calcium phosphate granules have pore sizes in the range of 0.5 to 6 mm.

4. The method according to claim 1 wherein the macroporous calcium phosphate granules have pore sizes in the range of 2 to 3 mm.

5. The method according to claim 1 wherein the porosity of the granules is 30 to 70%.

6. The method according to claim 1 wherein the porosity of the granules is 40 to 50%.

7. The method according to claim 1 wherein the calcium phosphate powder is mixed with 60 to 65 wt % sodium chloride powder.

8. The method according to claim 1 wherein 60 to 70 wt % of sodium chloride powder having particle sizes less than 0.25 mm and the remaining 30 to 40 wt % having particle sizes greater than 0.25 mm.

9. The method according to claim 1 wherein the macropores of the granules have middle diameters of 50 to 1000 microns.

10. The method according to claim 1 wherein the macropores of the granules have middle diameters of 50 to 400 microns.

11. A method according to claim 1, wherein the weight ratio of sodium chloride to calcium phosphate self-setting cement powder is from 1.7 to 1.8.

12. A method according to claim 11, wherein the weight ratio of sodium chloride to calcium phosphate self-setting cement powder is about 1.75.

* * * * *